United States Patent
Mayhew et al.

(10) Patent No.: US 6,291,690 B1
(45) Date of Patent: *Sep. 18, 2001

(54) HYDROPHOBIC TAXANE DERIVATIVES

(75) Inventors: Eric Mayhew, Monmouth Junction; J. Craig Franklin, Princeton, both of NJ (US); Suresh Bhatia, New Delhi (IN); Paul A. Harmon, Newtown; Andrew S. Janoff, Yardley, both of PA (US)

(73) Assignee: The Liposome Company, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,366

(22) Filed: May 9, 2000

Related U.S. Application Data

(63) Continuation of application No. 08/753,650, filed on Nov. 27, 1996, now Pat. No. 6,118,011, which is a continuation of application No. 08/474,888, filed on Jun. 7, 1995, now Pat. No. 5,580,899, which is a continuation-in-part of application No. 08/369,817, filed on Jan. 9, 1995, now abandoned.

(51) Int. Cl.[7] .................................................. C07D 305/14
(52) U.S. Cl. ........................................ 549/510; 549/511
(58) Field of Search .................................. 549/510, 511

(56) References Cited

U.S. PATENT DOCUMENTS

| | | | |
|---|---|---|---|
| 4,960,790 | 10/1990 | Stella et al. | 514/449 |
| 5,015,744 | 5/1991 | Holton | 549/510 |
| 5,200,534 | 4/1993 | Rao | 549/510 |
| 5,534,499 | 7/1996 | Ansell | 514/25 |
| 5,580,899 | 12/1996 | Mayhew et al. | 549/510 |

FOREIGN PATENT DOCUMENTS

| | | | |
|---|---|---|---|
| 0 414 610 | 2/1991 | (EP) | C07C/233/83 |
| 0 522 958 | 1/1993 | (EP) | C07D/305/14 |
| 0 528 729 | 2/1993 | (EP) | C07C/269/06 |
| 0 558 959 | 2/1993 | (EP) | C07D/305/14 |
| 91/13053 | 9/1991 | (WO) | C07C/299/34 |
| 93/10076 | 5/1993 | (WO) | C07C/231/20 |
| 93/16059 | 9/1993 | (WO) | C07D/305/14 |

OTHER PUBLICATIONS

Borman, "Scientists Mobilize to Increase Supply of Anticancer Drug Taxol", Chemical & Engineering News, Sep. 2, 1991, 11–18.

Edgington, et al., "Taxol, Out of the Woods", Biotechnology, 9:933–938 (Oct. 1991).

Holton, et al., "First Total Synthesis of Taxol. 1. Functionalization of the B Ring", J. Am. Chem. Sos. 116:1597–1600, (1994).

Nicolau, "Design, synthesis and biological activity of protaxols", Nature, 364, 464–466, 1993.

Nicolau, et al., "jTotal Synthesis of Taxol", Nature, 367:630–634 (1994).

Rizzo, et al., "Analysis of anitcancer drugs in biological fluids: determination of taxol with application to clainical pharmacokinetics", J. Pharma. & Biomed. Anal. 8(2): 159 (1990).

Schiff, et al., "Promotion of microtubule assembly in vitro by taxol", Nature 277:665 (1979).

Schiff, "Taxol stabilizes microtubules in mouse fibroblast cells", Proc. Natl. Acad. Sci. USA, 77(3):1561–1565, 1980.

Seydel, et al., "Chemische Struktur und biologische Aktivitat von Wirkstoffen", pp 73–78 and 292–293 (1979).

Suffness and Cordel, "Antitutmor Alkloids," in: *The Alkaloids, vol. XXI*, Academic Press, New York, pp 5–18 (1985).

*Primary Examiner*—Ba K. Trinh
(74) *Attorney, Agent, or Firm*—Rosanne Goodman

(57) ABSTRACT

This invention provides a taxane derivative of the formula:

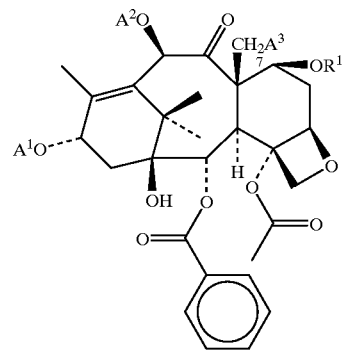

wherein a hydrophobic organic moiety is attached to a taxane. R and $R^1$ is each indepently H or a hydrophobic organic moiety, as long as at least one of R and $R^1$ is not H. Attachment of a hydrophobic organic moiety to the taxane so as to obtain a taxane derivative generally stabilizes the association of the derivative with a lipid, including a liposomal lipid, carrier in the plasma of animals to which the derivative-carrier association is administered. Also provided herein is a composition containing the taxane derivative and a pharmaceutically acceptable medium; desirably, the medium also contains a lipid carrier, and the derivative is associated with the carrier. Further provided herein is a method of administering taxane derivatives to animals, for example, animals afflicted with cancers.

10 Claims, 1 Drawing Sheet

HYDROPHOBIC TAXANE DERIVATIVES

This application is a continuation of U.S. Ser. No. 08/753,650, filed Nov. 27, 1996, now U.S. Pat. No. 6,118,011 which is a continuation of U.S. Ser. No. 08/474,888, filed Jun. 7, 1995, now U.S. Pat. No. 5,580,899, which is a continuation-in-part of U.S. Ser. No. 08/369,817, filed Jan. 9, 1995, now abandoned.

This invention provides a taxane derivative comprising a hydrophobic organic moiety attached to a taxane, compositions comprising such compounds, including lipid carrier-containing compositions, and methods of administering such compositions to animals, including those afflicted with cancers.

Taxanes can be anticancer agents, which affect cell growth by blocking cell division. Paclitaxel, for example, is an antimitotic agent which binds to tubulin, thereby blocking the disassembly of microtubules and consequently, inhibiting cell division (Schiff et al., Nature 277:665 (1979)). The optimal effect of paclitaxel on polymerization and stabilization of microtubuies is seen at concentrations near stoichiometric equivalence with tubulin dimers (Schiff and Horowitz, Proc. Natl. Acad. Sci. USA 77(3):1561–1565 (1980)). Paclitaxel has been found to have activity against ovarian and breast cancers, as well as against malignant melanoma,. colon cancer, leukemias and lung cancer (see, e.g., Borman, Chemical & Engineering News, Sep. 2, 1991, pp. 11–18; The Pharmacological Basis of Therapeutics * * * (Goodman Gilman et al, eds.) * * *, Pergamon Press, New York (1990), p. 1239; Suffness, Antitumor Alkaloids, in: "The Alkaloids, Vol. XXV," Academic Press, Inc. (1985), Chapter 1, pp. 6–18; Rizzo et al., J. Pharm. & Biomed. Anal. 8(2): 159–164 (1990); and Biotechnology 9:933–938 (October 1991).

Paclitaxel can be isolated from natural sources, or prepared synthetically frpm naturally occurring precursors, e.g., baccatin, by attachment of protecting groups to the hydroxyl groups of these precursors that are to become the hydroxyl groups of paclitaxel, converting the precursors, and then removing the protecting groups from the hydroxyl groups to obtain paclitaxel (see, e.g., WO93/10076, int. pub. date May 27, 1993; K. V. Rao, U.S. Pat. No. 5,200,534; R. A. Holton, U.S. Pat. No. 5,015, 744; PCT/US92/07990; V. J. Stella and A. E. Mathew, U.S. Pat. No. 4,960,790; K. C. Nicolau, Nature 364 (1993), pp. 464–466; Nicolaou, K. C. et al. Nature 367 (1994) pp.630–634; Holton, R. A., et al. J. Am. Chem. Soc. 116 (1994) pp. 1597–1600; WO93/16059, int. pub. date Aug. 19, 1993; EP 528,729, published Feb. 24, 1993; EP 522,958, published Jan. 13, 1993; WO91/13053, int. pub. date Sep. 5, 1991; EP 414,610, int. pub. date Feb. 27, 1991). The protecting groups used in some of these synthetic processes are short-chain aliphatic alkyl groups, but are not hydrophobic organic moieties as the term is used herein.

Paclitaxel is highly insoluble in water and aqueous solvents, and is currently supplied as an emulsion (TAXOL®, Bristol-Myers Squibb) in a polyoxyethylated derivative of castor oil and ethanol (CremophorEL®). However, administration of this formulation generally entails premedication with other drugs and a slow infusion of a large volume, to avoid toxicity associated with the Cremophor vehicle. Patients are therefore generally required to be admitted to hospitals over night. Compositions provided herein comprising a taxane derivative associated with a lipid carrier can solve this problem, by providing a formulation in which the taxane remains stably associated with the lipid carrier when administered. Stable association with a lipid carrier generally avoids the toxicity problems encountered with the currently used delivery system, as well as the need for slow-infusion administration.

SUMMARY OF THE INVENTION

This invention provides a taxane derivative of the formula:

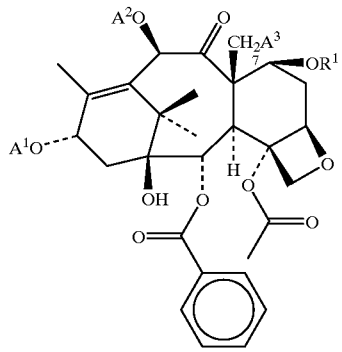

wherein: $A^1$ is H or a group having the formula Q—C(O)NHCH($C_6H_5$)CH(OR)C(O)—. Q is $C_6H_5$—, $(CH_3)_3CO$— or $(CH_3)CH=C(CH_3)$—; $A^2$ is H or $CH_3C(O)$—; $A^3$ is H, or OH. $A^1$ is preferably $(C_6H_5)(O)NHCH(C_6H_5)CH(OR)C(O)$—. Preferably, $A^2$ is $CH_3C(O)$—, and $A^3$ is H that is, the taxane derivative preferably is a paclitaxel.

When $R^1$ is H, $A^1$ is a group having the formula Q—C(O)NHCH($C_6H_5$)CH(OR)C(O)—; R is then not H, but rather, is a group having the formula $Y^1$, $Z^1X^1$ or $Z^1D^1$. When $A^1$ is H, or when $A^1$ is a group having the formula Q—C(O)NHCH($C_6H_5$)CH(OR)C(O)— and R is H, $R^1$ is then not H; rather, $R^1$ is then a group having the formula $Y^2$, $Z^2X^2$ or $Z^2D^2$. Accordingly, at least one hydrophobic organic moiety is attached to the taxane. Furthermore, two hydrophobic organic moieties can be attached to the taxane, R then being a group having the formula $Y^1$, $Z^1X^1$ or $Z^1 D^1$ when $R^1$ is a group having the formula $Y^2$, $Z^2X^2$ or $Z^2D^2$.

Each of $Y^1$ and $Y^2$ is independently a group having the formula: —C(O)$(CH_2)_a$(CH=CH)$_b$$(CH_2)_c$(CH=CH)$_d$$(CH_2)_e$(CH=CH)$_f$$(CH_2)_g$(CH=CH)$_h$$(CH_2)_i$$CH_3$. The sum of a+2b+c+2d+e+2f+g+2h+i is equal to an integer from 7 to 22 (refering to the number of carbon atoms); a is zero or an integer from 1 to 22; each of b, d, f and h is independently zero or 1; c is zero or an integer from 1 to 20; e is zero or an integer from 1 to 17; g is zero or an integer from 1 to 14; i is zero or an integer from 1 to 11; and a to i can be the same or different at each occurrence.

Each of $Z^1$ and $Z^2$ is independently a linker of the formula: —C(O)$(CH_2)_j$(CH=CH)$_k$$(CH_2)_l$(CH=CH)$_m$$(CH_2)_n$(CH=CH)$_o$$(CH_2)_p$(CH=CH)$_q$$(CH_2)_r$C(O)—. The sum of j+2k+l+2m+n+2o+p+2q+r is equal to an integer from 2 to 22; each of k, m, o and q is independently zero or 1; j is zero or an integer from 2 to 22; l is zero or an integer from 1 to 20; n is zero or an integer from 1 to 17; p is zero or an integer from 1 to 14; and r is zero or an integer from 1 to 11. Each of j to r can be the same or different at each occurrence.

Each of $X^1$ and $X^2$ is independently a group having the formula:

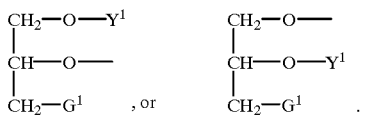

$G^1$ is —OP(O)$_2$OCH$_2$CH$_2$N(CH$_3$)$_3$ (phosphorylcholine), —OP(O)$_2$OCH$_2$CH$_2$NH$_2$, (phosphorylethanolamine) —OP(O)$_2$OCH$_2$CH(OH)CH$_2$OH (phosphorylglycerol), —OP(O)$_2$ OCH$_2$CH(NH$_2$)CO$_2$H (phosphorylserine) or phosphoylinositol.

Each of $D^1$ and $D^2$ is independently a group having the formula:

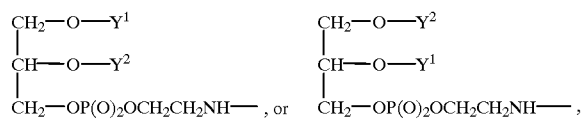

When R is not H, it is preferably a group having the formula $Y^1$. $Y^1$ is preferably a group having the formula —C(O)(CH$_2$)$_a$CH$_3$, and still more preferably, is —C(O)(CH$_2$)$_{10}$CH$_3$ or —C(O)(CH$_2$)$_{16}$CH$_3$. However, R can also be a group having the formula $Z^1X^1$. $G^1$ is then preferably phosphorylcholine, $Z^1$ is preferably —C(O)(CH$_2$)$_8$C(O)— and R is preferably a group having the formula:

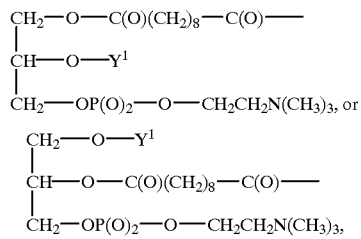

wherein $Y^1$ is preferably a group having the formula —C(O)(CH$_2$)$_a$CH$_3$.

R can further be $Z^1$ $D^1$. $Z^1$ is then preferably a group having the formula —C(O)(CH$_2$)$_j$C(O)—, more preferably, —C(O)(CH$_2$)$_3$C(O)—.

When $R^1$ is not H, it is preferably Y2. More preferably, $R^1$ is then a group having the formula —C(O)(CH$_2$)$_a$CH$_3$, and still more preferably, —C(O)(CH$_2$)$_{10}$CH$_3$ or —C(O)(CH$_2$)$_{16}$CH$_3$. However, $R^1$ can then also be a group having the formula $Z^2X^2$; $G^1$ is then preferably phosphorylcholine and $Z^2$ is preferably —C(O)(CH$_2$)$_8$C(O)—. $R^1$ can further be a group having the formula $Z^2D^2$; $Z^2$ is then preferably a group having the formula —C(O)(CH$_2$)$_j$C(O)—, more preferbly, —C(O)(CH$_2$)$_3$C(O)—.

Hydrophobic organic moieties can be attached to the same taxane at both the 2' and 7 positions; neither R nor $R^1$ is then H. R and $R^1$ can both be the same moiety, such as groups having the formula —C(O)(CH$_2$)$_{10}$CH$_3$ or —C(O)(CH$_2$)$_{16}$CH$_3$, or different moieties, but are preferably the same moiety.

Also provided herein is a composition comprising a pharmaceutically acceptable medium and the taxane derivative of this invention. The medium preferably comprises a lipid carrier, for example, a fatty acid, lipid, micelle, aggregate, lipoprotein or liposome, associated with the taxane. Preferably, the lipid carrier is a liposome. The lipid carrier can comprise an additional bioactive agent, that is, a bioactive agent in addition to the taxane derivative. Lipid carriers can also comprise a headgroup-modified lipid.

Further provided herein is a method of administering a taxane derivative to an animal, preferably a human. The method of this invention can be used to treat an animal afflicted with a cancer, by administering to the animal an anticancer effective amount of the derivative. "Anticancer effective" amounts of a taxane derivative are typically at least about 0.1 mg of the derivative per kg of body weight of the animal to which the derivative is administered; generally, the anticancer effective amount of the taxane is from about 0.1 mg per kg of body weight to about 1000 mg/kg. Preferably, the anticancer taxane derivative administered is a paclitaxel derivative.

DETAILED DESCRIPTION OF THE INVENTION

Figure 1:
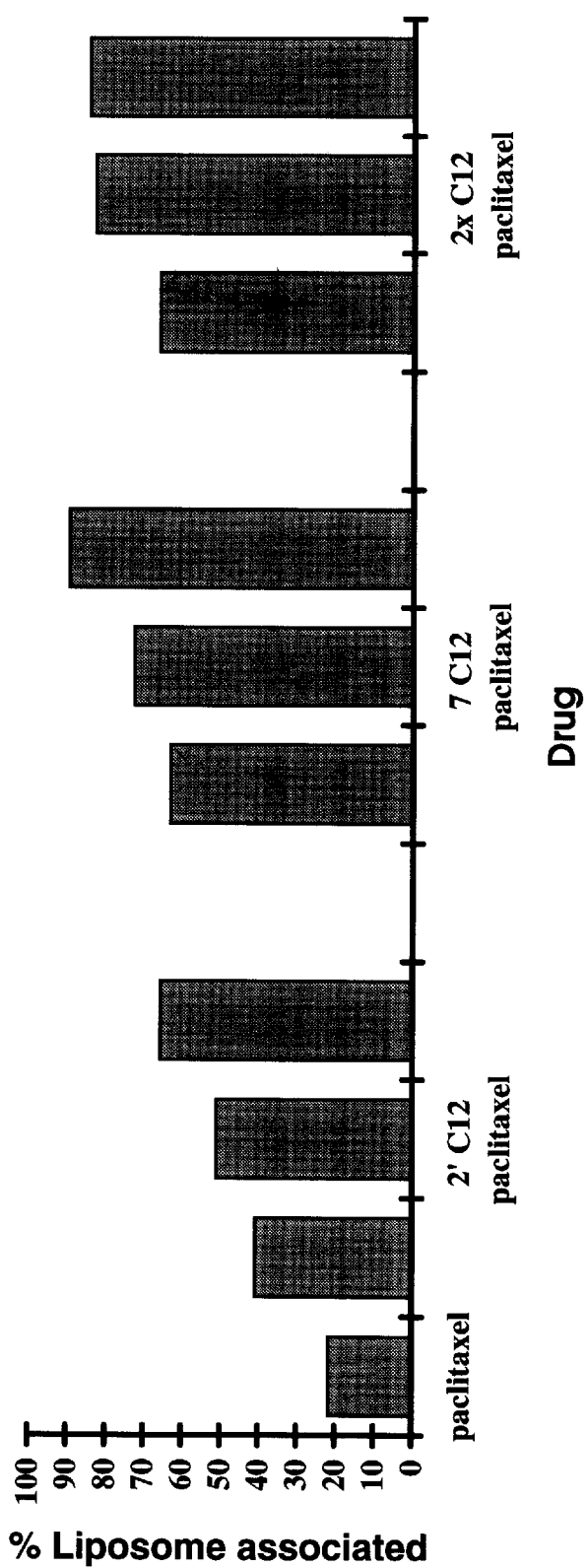
FIG. 1. Histograms reflecting association of paclitaxel and paclitaxel hydrophobic organic moiety conjugates with palmitoyloleoyl (POPC) liposomes. X-axis: paclitaxel; 2'—C12 paclitaxel (—C(O)(CH$_2$)$_{12}$CH$_3$ attached to paclitaxel at the 2' position); 7—C12 paclitaxel (—C(O)(CH$_2$)$_{12}$CH$_3$ attached to paclitaxel at the 7 position) and 2x—C12 paclitaxel (—C(O)(CH$_2$)$_{12}$CH$_3$ attached to paclitaxel at the 2' and 7 positions). Y-axis: percentage of paclitaxel associated with liposomes.

This invention provides a taxane derivative of the formula:

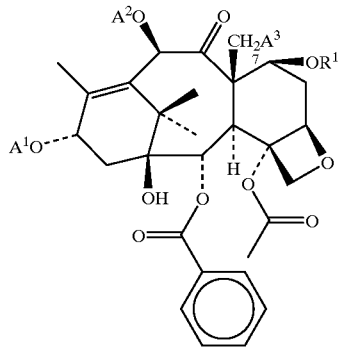

comprising a hydrophobic organic moiety attached to a taxane. $A^1$ is H or a group having the formula Q—C(O)NHCH(C$_6$H$_5$)CH(OR)C(O)—. Q is C$_6$H$_5$—, (CH$_3$)$_3$CO—, or CH$_3$CH=C(CH$_3$)—; $A^2$ is H or CH$_3$C(O)—; $A^3$ is H or OH.

$A^1$ is preferably a group having the formula Q—C(O)NHCH(C$_6$H$_5$)CH(OR)C(O)—; Q is then preferably C$_6$H$_5$, $A^2$ is then preferably CH$_3$C(O)— and $A^3$ is then preferably H. Accordingly, paclitaxel ([Compound I]); TAXOL® (C$_{47}$H$_{51}$NO), Bristol-Myers Squibb) is preferred herein. However, taxotere (II), which differs from paclitaxel by having a tert-butoxy carbonyl group at the C-13 position, instead of a benzoyl group, and a hydroxyl group, instead of an acetyloxy group, at C-10 is also useful herein. Accordingly, for taxotere, $A^1$ is (CH$_3$)$_3$COC(O)NHCH(C$_6$H$_5$)CH(OR)(O)—, $A^2$ is H, and $A^3$ is H. Cephalomannine (III), differs from paclitaxel in the amide group located at the distal end of the C-13 ester. $A^1$ is then (CH$_3$)CH=C(CH$_3$)C(O)NHCH(C$_6$H$_5$)CH(OR)C(O)—, $A^2$ is CH$_3$C(O)—and $A^3$ is H. Additional taxanes useful in accordance with the practice of this invention are known in the art and include, without limitation: 19-hydroxybaccatin III [IV] (McLaughlin, et al., J. Nat. Prod., 44:312–319 (1981)), Baccatin V [V], 10-deacetyl cephalomannine [VI], 10-deacetyl paclitaxel [VII], 7-Epi-10-deacetyl paclitaxel [VIII], 7-Epi-10deacetyl cephalomannine [IX], and 10-deacetyl baccatin III [X], as described in the following table, in addition to paclitaxel, taxotere and cephalomannine. The compound names listed are for unsubstituted, or "free", taxanes, that is, taxanes to which hydrophobic organic moieties are not attached.

| Compound | $A^1$ | $A^2$ | $A^3$ |
|---|---|---|---|
| Paclitaxel (I) | $C_6H_5C(O)NHCH(C_6H_5)CH(OR)C(O)$— | $CH_3C(O)$— | H |
| Taxotere (II) | $C(CH_3)_3OC(O)NHCH(C_6H_5)CH(OR)C(O)$— | H | H |
| Cephalo-mannine (III) | $(CH_3)CH=C(CH_3)C(O)NHCH(C_6H_5)CH(OR)C(O)$— | $CH_3C(O)$— | H |
| 19-hydroxy baccatin III (IV) | H | $CH_3C(O)$— | OH |
| Baccatin III (V) | H | $CH_3C(O)$— | H |
| 10-Deacetyl cephalo mannine (VI) | $(CH_3)CH=C(CH_3)C(O)NHCH(C_6H_5)CH(OR)C(O)$— | H | H |
| 10-Deacetyl taxol (VII) (7α-OH) | $C_6H_5C(O)NHCH(C_6H_5)CH(OR)C(O)$— | H | H |
| 7-Epi-10-deacetyl taxol(7β-OH) (VIII) | $C_6H_5C(O)NHCH(C_6H_5)CH(OR)C(O)$— | H | H |
| 7-Epi-10-deacetyl cephalo mannine(7β-OH) (IX) | $(CH_3)CH=C(CH_3)C(O)NHCH(C_6H_5)CH(OR)C(O)$— | H | H |
| 10-Deacetyl baccatin III (X) | H | H | H |

R and $R^1$ can each independently be either H or a hydrophobic organic moiety, as long as at least one of R and $R^1$ is not H. "Hydrophobic organic moieties" are carbon-based molecular groups which can be attached to taxanes. Free taxanes can readily dissociate from lipids with which they have been associated in the plasma of animals to which the taxane/lipid associations have been administered. Attachment of a hydrophobic organic moiety to a free taxane so as to obtain a taxane derivative can stabilize the association of the derivative with a lipid.

Hydrophobic organic moieties include, without limitation, saturated or unsaturated, aliphatic or branched fatty acids. Such moieties also include: polyol-, e.g., glycerol or mannitol, based amphipathic lipids comprising a polar group and one or more fatty acids. Furthermore, other hydrophobic organic moieties, including sphingolipids such as sphingomyelin, which can stabilize the association between a taxane derivative and a lipid in an animal's plasma can also be attached to a taxane according to the practice of this invention; selection of such other moieties is within the purview of ordinarily skilled artisans given the teachings of this invention.

"Attachment" means conjugation, covalent binding, linking, conjugation or otherwise forming a chemical connection between a taxane and a hydrophobic organic moiety. Attachment of the moiety is to one or more reactive groups, typically hydroxyl groups, on the taxane. Paclitaxel, for example, has three hydroxyl groups to which hydrophobic organic moieties can be attached. These are located at the 2', 7 and 1 positions, with their relative order of reactivity generally believed to be (from most reactive to least reactive) 2'>7>>1. Hydrophobic organic moieties can be attached to the primary reactive group of a taxane, e.g., the 2' OH group of paclitaxel, utilizing stoichiometric amounts of the moiety to be attached, e.g., fatty acid chlorides or anhydrides. Reactions are typically performed in the presence of a base, such as pyridine, dimethylaminopyridine, triethylamine, or others, and in commonly used polar, aprotic organic solvents. The progress of the reaction, at room temperature, can be monitored by a number of well known chromatographic means, for example, thin layer chromatography using a 3% methanol-in-chloroform solvent system. The compound's identity can be confirmed by spectroscopic and other analytical procedures, such as NMR spectroscopy.

Specific reaction and purification conditions are generally expected to vary according to a number of factors, including without limitation, the raw materials and reactants used, that are well within the purview of ordinarily skilled artisans to determine and control given the teachings of this invention. For example, for the attachment of lauric acid (C12) to paclitaxel, 9 mg (0.074 mmoles) dimethylaminopyridine (DMAP), 50 mg (0.059 mmole) of paclitaxel and 15 mg (0.068 mmoles) lauroyl chloride can be combined with 5 ml of chloroform.

Attaching hydrophobic organic moieties to less reactive groups on the taxane typically requires use of an amount of an active form of the moiety that is in excess of the stoichiometric amount. The hydroxyl group at the 7 position of paclitaxel, for example, can be modified, for example, by attaching a hydrophobic organic moiety to both the 2' and 7 OH groups, and then selectively removing the 2' moiety, such that the moiety at the 7 position remains attached to paclitaxel. Such reactions can be performed using essentially the same procedures as those described above. Selective removal of the 2' modification can be accomplished using stoichiometric amounts of a mild base, e.g., sodium bicarbonate.

Additionally, the 7 OH group of paclitaxel can be modified by "protecting" the 2' OH group before covalently linking the drug with the hydrophobic organic moiety. The 2' OH group can also be protected with groups such as, for example, triphenyl methyl, methoxytriphenyl methyl, trifluoroacetyl and hexanoyl groups, using processes generally known to ordinarily skilled artisans. The protected paclitaxel is then reacted with an active form of the moiety, e.g., fatty acid anhydrides or chlorides, in anhydrous organic solvent and bases such as DMAP and pyridine. The protecting group can be removed from the 2' position by well known and readily practiced means, under mildly acidic or basic conditions. Lauric acid can, for example, be attached to the 7 OH group of paclitaxel by combining 54 mg (0.44 mmoles) DMAP, 50 mg (0.059 mmoles) paclitaxel, and 77 mg (0.35 mmoles) of lauroyl chloride with 5 ml of chloroform, keeping the reaction at room temperature, so as to obtain 2'7-dilauroyl paclitaxel. Then, 3.0 mg NaCl in 75 microliters of water can be added to a solution of chloroform/methanol (1:1) containing 58 mg (0.048 mmoles) of 2'7-dilauroyl paclitaxel to remove the lauric acid attached to the 2'-OH group. This reaction can be incubated at 30 degrees C. and followed closely by thin layer chromatography (TLC). Attachment, however, is not limited to use of these specific amounts; rather, ordinarily skilled artisans can vary the amounts for reasons, and within ranges, well known to them, given the teachings of this invention.

R can be H or a group having the formula $Y^1$, $Z^1X^1$ or $Z^1D^1$; $R^1$ can be H, or a group having the formula $Y^2$, $Z^2X^2$ or $Z^2D^2$. At least one of R and $R^1$ is not H. $Y^1$, $Z^1X^1$, $Z^1D^1$, $Y^2$, $Z^2X^2$ and $Z^2D^2$ are hydrophobic organic moieties.

Each of $Y^1$ and $Y^2$ is independently a group having the formula: —$C(O)(CH_2)_a(CH=CH)_b(CH_2)_c(CH=CH)_d$ $(CH_2)_e(CH=CH)_f(CH_2)_g(CH=CH)_h(CH_2)_iCH_3$. The sum of $a+2b+c+2d+e+2f+g+2h+i$ is equal to an integer from 7 to 22 (refering to the number of carbon atoms); a is zero or an integer from 1 to 22; each of b, d, f and h is independently zero or 1; c is zero or an integer from 1 to 20; e is zero or an integer from 1 to 17; g is zero or an integer from 1 to 14; i is zero or an integer from 1 to 11; and a to i can be the same or different at each occurrence. Preferably, each of $Y^1$ and $Y^2$ is independently saturated, that is, there are no double bonds between adjacent carbon atoms. Accordingly, b, d, f and h are each preferably zero, c, e, g, and i are each also zero, and $Y^1$ and $Y^2$ are each independently groups having the formula $—C(O)(CH_2)_aCH_3$, wherein a is an integer from 7 to 22. More preferably, each of $Y^1$ and $Y^2$ is independently $—C(O)(CH_2)_{10}CH_3$ or $—C(O)(CH_2)_{16}CH_3$. Alternatively, $Y^1$ and $Y^2$ can each be unsaturated, that is, they can have one or more CH=CH groups. In this case, at least one of b, d, f or h is not zero. For example, when the unsaturated hydrocarbon has one double bond: b is 1, d, f and h being zero; $Y^1$ and $Y^2$ are each then independently a group having the formula $—C(O)(CH_2)_aCH=CH(CH_2)_cCH_3$; a is zero or an integer from 1 to 18; c is also zero or an integer from 1 to 18, at least one of a or c is not zero, and the sum of a and c is equal to an integer of from 5 to 20.

$X^1$ and $X^2$ are each independently a group having the formula:

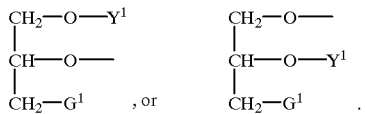

$G^1$ is preferably a phosphate-based polar group, including without limitation: $—OP(O)_2OCH_2CH_2N(CH_3)_3$ (phosphorylcholine), $—OP(O)_2OCH_2CH_2NH_2$ (phosphorylethanolamine) $—OP(O)_2OCH_2CH(OH)CH_2OH$ (phosphorylglycerol), $—OP(O)_2OCH_2CH(NH_2)CO_2H$ (phosphorylserine) and phosphorylinositol. More preferably, $G^1$ is phosphorylcholine. However, nitrogen, sulfur and other atoms can be substituted for the phosphorous. $Y^1$ is preferably a group having the formula $—C(O)(CH_2)_aCH_3$.

Each of $Z^1$ and $Z^2$ is independently a linker of the formula: $—C(O)(CH_2)_j(CH=CH)_k(CH_2)_l(CH=CH)_m(CH_2)_n(CH=CH)_oCH_2)_p(CH=CH)_q(CH_2)_rC(O)—$. The sum of $j+2k+l+2m+n+2o+p+2q+r$ is equal to an integer of from 2 to 22; each of k, m, o and q is independently zero or 1; j is zero or an integer from 2 to 22; l is zero or an integer from 1 to 20; n is zero or an integer from 1 to 17; p is zero or an integer from 1 to 14; and r is zero or an integer from 1 to 11. Each of j to r can be the same or different at each occurrence. Preferably, each of $Z^1$ and $Z^2$ is independently a group having the formula $—C(O)(CH_2)_jC(O)—$, more preferably, each of $Z^1$ and $Z^2$ is $—C(O)(CH_2)_8C(O)—$.

$D^1$ and $D^2$ are each independently:

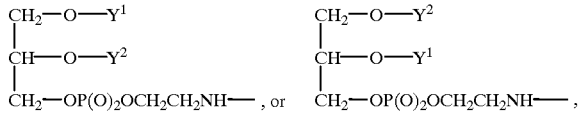

$Y^1$ and $Y^2$ are then preferably and independently each a group having the formula $—C(O)(CH_2)_aCH_3$. For example, both $Y^1$ and $Y^2$ can each be $—C(O)(CH_2)_{14}CH_3$.

When $R^1$ is H, $A^1$ is a group having the formula $Q—C(O)NHCH(C_6H_5)CH(OR)C(O)—$, and R is not H. R is then a group having the formula $Y^1$, $Z^1X^1$, or $Z^1D^1$, and the taxane derivative comprises a hydrophobic organic moiety attached at the 2' position of the taxane. When $A^1$ is H, or when $A^1$ is a group having the formula $Q—C(O)NHCH(C_6H_5)CH(OR)C(O—$ and R is H, then $R^1$ is not H. $R^1$ is then $Y^2$, $Z^2X^2$ or $Z^2D^2$, and the taxane derivative has a hydrophobic organic moiety attached at the 7 position. Alternatively, the taxane derivative can have a hydrophobic organic moiety attached at both the 2' and the 7 positions of the taxane; these moieties can be the same or different at each occurence, but are preferably the same. R is then a group having the formula $Y^1$, $Z^1X^1$, or $Z^1D^1$ when $R^1$ is a group having the formula $Y^2$, $Z^2X^2$, or $Z^2D^2$.

Also provided herein is a composition comprising the taxane derivative of this invention and a pharmaceutically acceptable medium; such a medium preferably comprises a lipid carrier associated with the taxane derivative. "Pharmaceutically acceptable media" are generally intended for use in connection with the administration of active ingredients to animals, for example, humans, and include solids, such as pills, capsules and tablets, gels, excipients or aqueous or nonaqueous solutions. Active ingredients can, for example, be combined with, dissolved, suspended, or emulsified in or with such media. Pharmaceutically acceptable media are generally formulated according to a number of factors well within the purview of the ordinarily skilled artisan to determine and account for, including without limitation: the particular active ingredient used, its concentration, stability and intended bioavailability; the disease, disorder or condition being treated with the composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, J. G. Nairn, in: *Reminaton's Pharmaceutical Science* (A. Gennaro, ed.), Mack Publishing Co., Easton, Pa., (1985), pp. 1492–1517). Typical pharmaceutically acceptable media used in parenteral drug administration include, for example, D5W, an aqueous solution containing 5% weight by volume of dextrose, and physiological saline. Pharmaceutically acceptable media can contain additional ingredients which enhance the stability of the active ingredients, including preservatives and anti-oxidants.

A "lipid carrier" is a a hydrophobic substance, or an amphipoathic substance having a hydrophobic domain, with which the taxane derivative of this invention can form a stable association, and which is suitable for therapeutic administration to animals. "Association" as used herein generally means association between the hydrophobic organic moiety attached to the taxane and the hydrophobic portion of the lipid carrier. Hydrophobic organic moieties and hydrophobic lipid domains generally associate through the action of a number of forces, such as Van der Waal's forces, generally known to operate between hydrophobic molecules in an aqueous environment. Means of determining the stability of such associations, for example, by determining the percentage of taxane derivative recoverable with phosphorous when the lipid carrier comprises a phospholipid, are well known to, and readily practiced by, ordinarily skilled artisans given the teachings of this invention. Ordinarily skilled artisans can, given the teachings of this invention, select suitable lipid carriers. These include, without limitation: fatty acids, amphipathic lipids, liposomal or nonliposomal, lipoproteins and others. Preferably, the lipid carrier with which the taxane derivative of this invention is associated is a liposome.

Liposomes comprise one or more bilayers of lipid molecules, each bilayer encompassing an aqueous compartment. Unilamellar liposomes have a single lipid bilayer and multilamellar liposomes have more than one bilayer (for a review see, for example, see Chapman, "Physicochemical Properties of Phospholipids and Lipid-Water Systems," in: *Liposome Technology, Volume I: Preparation of Liposomes* (G. Gregoriadis, ed.). CRC Press, Boca Raton, Fla. (1984), pp. 1–18, the contents of which are incorporated herein by reference). The amphipathic lipid molecules which make up lipid bilayers comprise a polar (hydrophilic) headgroup and one or two acyl chains. The polar groups can be phosphate-, sulfate or nitrogen-based groups, but are preferably phosphate groups, such as phosphorylcholine, phosphorylethanolamine, phosphorylserine, phosphorylglycerol or phosphorylinositiol. The fatty acids generally comprise from 4 to 24 carbon atoms, and can be saturated (e.g., myristic, lauric, palmitic, or stearic acids, or unsaturated (e.g., oleic, linoleic, linoleic and arachidonic acid). Furthermore, liposomes can also comprise sterols, such as cholesterol, and other lipids.

Liposomes can be made by a variety of methods, including: Bangham's methods for making muiltilamellar liposomes (MLVs); Lenk's, Fountain's and Cullis' methods for making MLVs with substantially equal interlamellar solute distribution; extrusion, sonication or homogenization of MLVs to make unilamellar liposomes; and ether or ethanol injection processes (see, for example, U.S. Pat. Nos. 4,522, 803, 4,588,578, 5,030,453, 5,169,637 and 4,975,282, and R. Deamer and P. Uster, "Liposome Preparation: Methods and Mechanisms," in *Liposomes* (M. Ostro, ed.), Marcel Dekker, Inc., New York (1983), pp. 27–52, the contents of which are incorporated herein by reference).

Lipid carriers associated with the taxane derivative of this invention, for example, liposomes, can comprise an additional bioactive agent, that is, a bioactive agent in addition to the taxane derivative. Liposomes, for example, can be loaded with biologically active agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056, and U.S. Ser. No. 08/112,875, the contents of which are incorporated herein by reference).

Lipid carrier/bioactive agent formulations can enhance the therapeutic index of the bioactive agent, for example by buffering the agent's toxicity and by reducing the rate at which the agent is cleared from the circulation of animals, thereby meaning that less of the agent need be administered to achieve the desired therapeutic effect. In this regard, lipid carriers, for example, liposomes, can also comprise one or more headgroup-modified lipids, which are amphipathic lipids whose polar headgroups have been derivatized by attachment thereto of a chemical moiety, e.g., polyethylene glycol, a polyalkyl ether, a ganglioside, an organic dicarboxylic acid or the like, which can inhibit the binding of serum proteins to lipid carriers such that the pharmacokinetic behavior of the carriers in the circulatory systems of animals is altered (see, e.g., Blume et al., Biochim. Biophys. Acta. 1149:180 (1993); Gabizon et al., Pharm. Res. 10(5): 703 (1993); Park et al. Biochim. Biophys Acta. 1108:257 (1992); Woodle et al., U.S. Pat. No. 5,013,556; Allen et al., U.S. Pat. Nos. 4,837,028 and 4,920,016; U.S. Ser. No. 142,691, filed Oct. 25, 1993). Lipid carriers are generally cleared from animals' circulations by their reticuloendothelial systems (RES). Avoiding RES clearance can allow the carriers to remain in the circulation longer, meaning that less of the associated drug need be administered to achieve desired serum levels. Enhanced circulation times can also allow targeting of liposomes to non-RES containing tissues. The hydrophobic organic moiety attached to the taxane can also be a headgroup-modified lipid.

The amount of the headgroup-modified lipid incorporated into the carrier depends upon a number of factors well known to the ordinarily skilled artisan, or within his purview to determine without undue experimentation. These include, but are not limited to: the type of lipid and the type of headgroup modification; the type and size of the carrier; and the intended therapeutic use of the formulation. The concentration of the headgroup-modified lipid in the carrier is generally sufficient to prolong the circulatory half-life of the carrier in an animal, but is not so great as induce unwanted side effects in the animal, and is typically at least about five mole percent of the lipid present in the carrier, The preferred headgroup-modified lipid is dipalmitoyl phosphatidylethanolamine-glutaric acid (DPPE-GA), which is typically used at a concentration of about 10 mole percent of the lipid present.

"Bioactive agent" as used herein denotes any compound or composition of matter which can be administered to animals and which can have biological or diagnostic actiovity therein. Bioactive agents include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, purine and pyrimidine analogs; antineoplastic agents such as the anthracycline antibiotics and plant alkaloids; such as cholesterol; carbohydrates, e.g., sugars and starches, amino acids, peptides, proteins such as cell receptor proteins, immunoglobulins, enzymes, hormones, neurotransmitters and glycoproteins; dyes; radiolabels such as radioisotopes and radioisotope-labelled taxanes; radiopaque taxanes; fluorescent taxanes; mydriatic taxanes; bronchodilators; local anesthetics; and the like. The additional bioactive agent used herein is preferably an antimicrobial or antineoplastic agent. The additional bioactive agent can be a therapeutic lipid, such as a ceramide. The additional agent can also be a second taxane derivative.

Further provided herein is a method of administering a taxane derivative to an animal, e.g., a human. The method comprises administering to the animal a composition comprising the derivative and a pharmaceutically acceptable medium. The medium preferably comprises a lipid carrier, more preferably a liposome, associated with the taxane derivative. The taxane derivative used in the method of this invention comprises a hydrophobic organic moiety attached to a taxane, and has the formula:

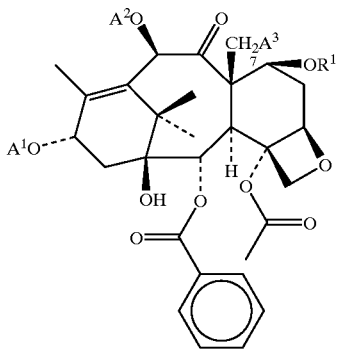

A¹ is H or a group having the formula Q—C(O)NHCH(C₆H₅)CH(OR)C(O)—; Q is C₆H₅—, (CH₃)₃C—O— or (CH₃)CH=C(CH₃)—; A² is H or CH₃C(O)—; A³ is H or OH; R is H, or a group having the formula $Y^1$, $Z^1X^1$, or $Z^1D^1$; and $R^1$ is H, or a group having the formula $Y^2$, $Z^2X^2$, or $Z^2D^2$. When $R^1$ is H, A¹ is a group having the formula Q—C(O)NHCH(C₆H₅)CH(OR)C(O)— and R is not H; when A¹ is H or when A¹ is a group having the formula Q—C(O)NHCH(C₆H₅)CH(OR)C(O)—$R^1$ is not H; and, at least one of R and $R^1$ is not H. When $R^1$ is H, R is preferably a group having the formula $Y^1$. When A¹ is H, or when R is H, $R^1$ is preferably a group having the formula $Y^2$.

Each of $Y^1$ and $Y^2$ is independently a group having the formula $C(O)(CH_2)_a(CH=CH)_b(CH_2)_c(CH=CH)_d(CH_2)_e(CH=CH)_f(CH_2)_g(CH=CH)_h(CH_2)_iCH_3$. The sum of $a+2b+c+2d+e+2f+g+2h+i$ is equal to an integer 22; a is zero or an integer from 1 to 22; each of b, d, f and h is independently zero or 1; c is zero or an integer from 1 to 20; e is zero or an integer from 1 to 17; g is zero or an integer from 1 to 14; i is zero or an integer from 1 to 11; and a to i can be the same or different at each occurrence. Each of $Y^1$ and $Y^2$ is preferably, and independently, a group having the formula $—C(O)(CH_2)_aCH_3$. When R is a group having the formula $Y^1$, and when $R^1$ is a group having the formula $Y^2$, each is independently preferably $—C(O)(CH_2)_{10}CH_3$ or $C(O)(CH_2)_{16}CH_3$.

Each of $X^1$ and $X^2$ is independently a group having the formula:

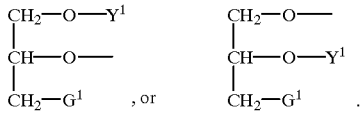

$G^1$ is $—OP(O)_2OCH_2CH_2N(CH_3)_3$, $—OP(O)_2OCH_2CH_2NH_2$, $—OP(O)_2OCH_2CH(OH)CH_2OH$, or $—OP(O)_2OCH_2CH(NH_2)CO_2H$.

Each of $Z^1$ and $Z^2$ is independently a linker of the formula: $—C(O)(CH_2)_j(CH=CH)_k(CH_2)_lCH=CH)_m(CH_2)_n(CH=CH)$ $OCH_2)_p(CH=CH)_q(CH_2)C(O)—$. The sum of $j+2k+l+2m+n+2o+p+2q+r$ is equal to an integer from 2 to 22; each of k, m, o and q is independently zero or 1; j is zero or an integer from 2 to 22; l is zero or an integer from 1 to 20; n is zero or an integer from 1 to 17; p is zero or an integer from 1 to 14; r is zero or an integer from 1 to 11 and each of j to r can be the same or different at each occurrence. Preferably, each of $Z^1$ and $z^2$ independently has the formula: $—C(O)(CH_2)_jC(O)—$; more preferably, each of $Z^1$ and $Z^2$ is $—C(O)(CH_2)_8C(O)—$.

Each of $D^1$ and $D^2$ is independently a group having the formula:

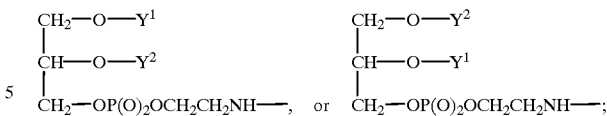

Preferably, each of $Y^1$ and $Y^2$ is then independently a group having the formula $—C(O)(CH_2)_aCH_3$, for example, $—C(O)(CH_2)_{14}CH_3$.

Animals afflicted with cancers can be treated according to the method of this invention, by administration of an anticancer effective amount of a taxane derivative provided herein. Paclitaxel derivatives are preferred for use herein. Generally, those cancers treatable by the method of this invention are those which may be treated with the corresponding free, i.e., unattached taxane, and include, without limitation: carcinomas, myelomas, neuroblastomas, or sarcomas, of the brain, breast, lung, colon, prostate or ovaries, as well as leukemias or lymphomas.

Anticancer activity of taxane derivatives can be examined in vitro, for example, by incubating a cancer cell culture with the derivative, and then evaluating cell growth inhibition in the culture. Suitable cells for such testing include murine P388 leukemia, B16 melanoma and Lewis lung cancer cells, as well as human mammary MCF7, ovarian OVCAR-3 and A549 lung cancer cells. $GI_{50}$ values, that is, the concentration of a taxane derivative required to induce 50% cell growth inhibition in a culture, for a derivative can be determined and compared. The lower a taxane derivative's $GI_{50}$, the lower is the amount of the derivative required to inhibit cancer cell growth. Accordingly, compounds with lower $GI_{50}$'s can have better therapeutic indices.

Alternatively, a taxane derivative can be tested in vivo for antitumor activity, for example, by first establishing tumors in suitable test animals, e.g., nude mice. Cells suitable for establishing tumors include those described above for in vitro testing, as well as other cells generally accepted in the art for establishing tumors. Subsequently, the taxane derivative is administered to the animal; $ED_{50}$ values, that is, the amount of the derivative required to achieve 50% inhibition of tumor growth in the animal are then determined, as are survival rates. Ordinarily skilled artisans, given the teachings of this invention, are well able to select particular taxane derivatives for application against certain cancers, on the basis of such factors as $GI_{50}$, $ED_{50}$ and survival values.

For the purposes of this invention, an "anticancer effective amount" of a taxane derivative is any amount of the derivative effective to ameliorate, lessen, inhibit or prevent the establishment, growth, metastasis, invasion or spread of a cancer. Anticancer effective amounts of taxane derivatives of this invention can be the same amount as therapeutic doses of the corresponding free taxane. However, the attachment of a hydrophobic organic moiety to the taxane so as to obtain a taxane derivative, and the association of this derivative with a lipid, e.g., a liposome, in a carrier, can enhance the drug's therapeutic index. Accordingly, this can mean that less of the taxane derivative, in comparison to the free taxane, need be used to achieve the desired therapeutic effect, and accordingly, that anticancer effective amounts of the derivative can be less than anticancer effective amounts of the free taxane.

Anticancer effective amounts of taxane derivatives can be chosen in accordance with a number of factors, e.g., the age, size and general condition of the subject, the cancer being treated and the intended route of administration of the derivative, and determined by a variety of means, for example, dose ranging trials, well known to, and readily practiced by, ordinarily skilled artisans given the teachings of this invention. Generally, the anticancer effective amount of the taxane derivative of this invention is at least about 0.1 mg of the derivative per kg of body weight of the animal to which the composition is administered. Preferably, the anticancer effective amount of the taxane derivative is from about 0.1 mg per kg to about 1000 mg per kg.

Furthermore, the method provided herein can comprise administering an additional bioactive agent, typically an antineoplastic agent, to the animal. This additional bioactive agent can be administered to an animal prior to, concurrently with or subsequently to administration of the taxane derivative of this invention. The additional agent can be entrapped in a liposome, for example, the same liposome with which the taxane derivative of this invention can be associated.

This invention will be better understood from the following Examples. However, those of ordinary skill in the art will readily understand that these examples are merely illustrative of the invention as defined in the claims which follow thereafter.

EXAMPLES

Example 1

Synthesis of Taxanes

2' caproyl-paclitaxel

Paclitaxel (100 mg, 0.117 mmoles), dimethylaminopyridine (DMAP), (18 mg, 0.133 mmoles), and 10 ml of chloroform were combined in an oven-dried, 50-ml round-bottom flask with 18 mg (0.147 mmoles) of caproyl chloride, and incubated at room temperature. Reaction progress was monitored by silica-based thin layer chromatography (TLC), using a 3% methanol-in-chloroform solvent system. By 4 hours, the spot corresponding to paclitaxel ($R_f=0.3$) was no longer evident; a spot not present in the analysis of the initial reaction mixture ($R_f=0.5$) was present.

Water (25 ml) was added to the reaction, and then extracted into chloroform to remove most of the DMAP. After drying with magnesium sulfate, material from the chloroform phase was dissolved in 1% methanol in chloroform. The dissolved material was then added to a plug of silica Gel 60 (Fluka Fine Chemicals) 4 cm high×4 cm diameter, and 300 ml of a 1% methanol-in-chloroform mixture was run through the plug.

The resulting compound was identified as 2' caproyl-paclitaxel(paclitaxel in which $CH_3(CH_2)_4C(O)-$ was attached to the 2'—OH group of paclitaxel) by NMR spectroscopy (see below).

7 Lauroyl-Paclitaxel

Paclitaxel (50 mg, 0.059 mmoles), DMAP (54 mg, 0.44 mmoles), lauroyl chloride (77 mg, 0.35 mmoles), and 5 ml of chloroform were combined in a 50 ml round-bottom flask, and incubated at room temperature. Reaction progress was monitored as described above. At 4 hours of incubation, the spot corresponding to paclitaxel was no longer present, the spot corresponding to 2' lauroyl-paclitaxel ($R_f=0.5$) was the largest, and another spot ($R_f=0.7$) began to appear. At 24 hours, the spot corresponding to 2' lauroyl-paclitaxel had disappeared, and the spot ($R_f=0.7$) corresponding to paclitaxel acetylated at both the 2' and 7 positions had increased in size.

The reaction was then extracted, and run through a silica plug, as described above. Flash chromatography, using a solvent system comprising 1.5% methanol-in-chloroform was used to separate the material at spot $R_f=0.7$ from the material running with the solvent front. The compound was identified as 2',7 di-caprolypaclitaxel by NMR spectroscopy.

Fifty-eight mg (0.048 mmoles) of the diacetylated material was combined with 4.2 mg of sodium bicarbonate dissolved in 75 ul of water, in 30 ml of chloroform/methanol (1:1). Reaction progress was assayed frequently, so as to minimize hydrolysis of other ester linkages on the molecule while hydrolyzing the 12 carbon residue present at the 2' position. At 8 hours, one major peak ($R_f=0.5$), and two minor peaks, ($R_f=0.55, 0.45$), were observed; however, most of the material in the reaction mixture appeared to be starting material. Further incubation did not substantially increase the major spot ($R_f=0.5$). Accordingly, 25 ml of water was added to the reaction mixture, and then extracted into chloroform. Preparative TLC chromatography (Whatman 20×20 c, fluorescent at @ 254 nm, 1000 micron plate) was used to purify the compounds. The compound was identified as 7 caproyl-paclitaxel by NMR spectroscopy.

NMR Spectroscopy $^1H$ and proton-decoupled $^{13}C$ spectra of paclitaxel reacted with 6, 12 and 18 carbon fatty acids were taken. Shifts in the resonance identified as being protons alpha to the hydroxyl groups are indicative of the of acylation of the corresponding hydroxyl group (see, for example, Kingston, Pharm. Ther. 52 (1991), pp. 1–34). Reactions with the 2' OH group proton are characterized by disappearance of resonance at 3.6 ppm and a shift of the proton alpha to the hydroxyl group from 4.8 ppm to 5.6 ppm. Similar changes were reported by Kingston upon acetylation of the 2' OH group.

Paclitaxel derivatized with fatty acids at the 2' and 7 positions show the same changes as occur with 2' derivatization, as well as loss of resonance at 2.5 ppm (7 OH group proton) and a resonance shift from 4.5 ppm to 5.65 ppm. Reactions with the 7 hydroxy proton are characterized disappearance of resonance at 2.5 ppm, and a shift of the proton alpha to the OH group from 4.5 to 5.65 ppm. Similar to changes were reported by Kingston with acetylation of the 7 OH group[1]. Carbon spectra of paclitaxel attached to a fatty acid have an additional resonance, in frequencies associated with the carbonyl functional group (165 to 200 ppm), as well as resonances in frequencies associated with aliphatic carbons (10 to 60 ppm).

Example 2

Association Assays

Liposomes were prepared, using the lipid concentrations indicated in the table below ("DSPC"=distearoyl phosphatidylcholine; "EPC"=egg phosphatidylcholine; "GA"= dipalmitoyl phosphatidylethanolamine/Glutaric Acid; "Chol"=cholesterol; "drug"=taxane derivative and standard procedures to make multilamellar liposomes; these were then extruded ten times through a filter having 100-nm pores so as to obtain unilamellar liposomes (see Cullis et al., U.S. Pat No. 5,008,050).

Paclitaxel and hydrophobic derivatives of paclitaxel were formulated in liposomes composed of POPC. 54.6 nanomoles of the liposomal formulation of each drug was passed through a 55 cm×3 cm column filled with BioGel A-15m. 200–400 mesh Bio-Rad agarose beads, at a flow rate of 6 cm/min.

Results are presented in FIG. 1. For paclitaxel approximately 20% of the drug remains associated with liposomes after passage through the column. However, for 7 caprolylpaclitaxel approximately 90% of the drug remains associated with liposomes.

Table 1, the "Summary of the Formulation Study Table," presented below is a summary of the results from several studies of the effect of the liposomal composition on 7 caproyl-paclitaxel and 7 stearoyl-paclitaxel. In particular, effects of saturation, cholesterol and PE-GA inclusion were examined. Column 1 describes the liposomal formulation examined, column 2 the amount of drug associated with liposomes after passage through gel filtration columns (as described above), column 3 is a qualitative index of liposome aggregation (as observed by microscopy), and column 4 the mole percent of taxane associated with lipid after liposome formation and extrusion through 100 nm filters. Unless otherwise stated, initial paclitaxel concentration was 5 mole percent.

TABLE 1

SUMMARY OF FORMULATION STUDY

| FORMULATION | % RETAINED Avg. | Std. Dev. | AGG. | % drug post extrusion |
|---|---|---|---|---|
| 7 Stearoyl-paclitaxel | | | | |
| DSPC; 10% GA; 5% Drug | 49 | 1 | — | 4 |
| EPC; 10% GA; 5% Drug | 78 | 14 | — | 3 |
| EPC; 25% CHOL; 5% Drug | 129 | 25 | *** | 4 |
| 7 caproyl-paclitaxel | | | | |
| EPC; 20% GA; 15% Drug | 56 | 10 | — | 12 |
| EPC; 10% GA; 15%; Drug | 44 | 7 | — | 14 |
| EPC; 10% GA; 5% Drug | 37 | 11 | — | 8 |
| EPC; 25% CHOL; 5% Drug | 31 | 1 | ** | 6 |
| EPC; 25% CHOL; 10% GA; 5% Drug | 43 | 11 | * | 6 |
| DSPC; 10% GA; 5% Drug | 61 | 20 | — | 3 |
| DSPC; 25% CHOL; 5% Drug | 45 | | **** | 1 |
| DSPC; 25% CHOL; 10% GA; 5% Drug | 30 | | ** | 1 |

Example 3
Characterization of Taxane-Containing POPC Lirosomes

Palmitoyloleoyl phosphatidylcholine (POPC) liposomes containing either paclitaxel itself or a taxane-hydrophobic organic moiety conjugate were prepared at a mole ratio of 95:5, lipid:drug according to procedures described hereinabove. The lipid, conjugate and paclitaxel concentrations were determined after liposome preparation, as well as before and after passing through a size exclusion column (200–400 mesh Bio-Rad agarose beads). The decrease, if any, in the association of paclitaxel or the conjugate with the POPC was calculated and used as a measure of association with liposomes. Results are presented in Table 2, below.

TABLE 2

LIPOSOME ASSOCIATION STUDIES

| Compound | % Taxane Associated with Liposomes |
|---|---|
| 2'-caproyl paclitaxel | 40.8 |
| 2'-lauroyl paclitaxel | 50.9 |
| 2'-stearoyl paclitaxel | 65.7 |
| 7-caproyl paclitaxel | 63.2 |
| 7-lauroyl paclitaxel | 72.6 |
| 7-stearoyl paclitaxel | 89.5 |
| Paclitaxel | 21.7 |

Example 4
In Vivo Studies

Liposomes were made, with dipalmitoyl phosphatidylcholine (DSPC), distearoyl phosphatidylethanolamine-glutaric acid (DPPE-GA) and 7-caproyl paclitaxel (7-C6), according to procedures described hereinabove at a molar ratio of DSPC:DPPE-GA:7-C6 of 8:1:0.6.

P-388 Studies

Groups of mice were injected with $1\times10^5$ P388 cells and then, 24 hours later, either Taxol® (cremophor-based paclitaxel suspension) or a taxane-containing liposome. "Plain," that is, non-taxane-containing, liposomes were administered at 512 mg/kg of body weight, which was equivalent to a 50 mg/kg dose of the taxane-containing liposomes. Liposome, or Taxol®, administration was repeated at days 2, 3, 4 and 5 post cell administration. Days of death were then observed, and mean survival times calculated. These data are presented in Table 3, below.

TABLE 3

SURVIVAL OF P388 TUMOR-BEARING MICE

| Treatment | Dose (mg/kg) | Mean Survival Time, Days (# mice) | ILS[1] as of Control |
|---|---|---|---|
| PBS[2] | 0.2 ml | 11.6 ± 0.2 (5) | — |
| Plain Liposomes | 512 mg/kg | 11.2 ± 0.2 (5) | (−)3.5 |
| 7-C6 Liposomes | 50 | 17.2 ± 0.7 (5) | 48.2 |
| 7-C6 Liposomes | 25 | 13.2 ± 0.2 (10) | 13.8 |
| Taxol ® | 12.5 | 17.6 ± 0.8 (10) | 51.7 |

[1]: "ILS" = increased life span = ((mean survival time (MST)treatment group/MST control) × 100) − 100;
[2]: phosphate buffered saline.

B-16 Studies

Groups of mice were injected (intravenously) with $1\times10^5$ B-16 cells, and then, one day later, either PBS, plain liposomes, Taxol®, or 7-C6 liposomes. Treatment was repeated on days 3, 5, 7 and 9 post-cell administration. On day 21, the animals were sacrificed, and their lungs were removed and fixed in formalin. The number of melanotic lung nodules was counted "blind" using a magnifier; data is presented in Table 4, below.

TABLE 4

EFFECT ON DEVELOPMENT OF B16 MELANOMA LUNG TUMORS

| Treatment | Dose (mg/kg) | Mean Number of Tumor Nodules (# mice) | % Reduction in Nodule # vs. PBS-Control |
|---|---|---|---|
| PBS[2] | 0.2 ml | 27.1 ± 2.6 (8) | — |
| Plain Liposomes | 512 mg/kg | 28.6 ± 1.4 (8) | (−)5.5 |
| 7-C6 Liposomes | 50 | 11.4 ± 1.2 (8) | 57.9 |
| 7-C6 Liposomes | 25 | 13.3 ± 2.3 (8) | 50.9 |
| Taxol ® | 12.5 | 17.5 ± 2.7 (8) | 35.4 |

Example 5

Growth Inhibition Studies

Cells (A549, MCF7 or Lewis Lung) were incubated with various concentrations of paclitaxel; cell growth inhibition was determined by standard means. Results of these experiments are presented in Tables 5 and 6 (below), with the data there indicating the concentration ($GI_{50}$), micromolar, of either free paclitaxel, or a free paclitaxel derivative (Table 5) or liposomal paclitaxel or derivative (Table 6), that is, the concentration found to inhibit about fifty percent of the growth of the indicated cell lines.

TABLE 5

GROWTH INHIBITION BY THE PACLITAXEL AND IT'S DERIVATIVES

| Compound | Cell Line A549 | MCF7 | LEWIS LUNG |
|---|---|---|---|
| Paclitaxel | 0.004 +/− 0.0001 | 0.004 +/− 0.0001 | 0.031 +/− 0.012 |
| 2'-C6 | 0.41 +/− 0.134 | 0.50 +/− 0.151 | 1.22 +/− 0.592 |
| 2'-C12 | 0.45 +/− 0.08 | 0.84 +/− 0.17 | 1.26 +/− 0.87 |
| 2'-C18 | 7.56 +/− 1.513 | >6.0 | >10 |
| 2',7-diC6 | >10 | >10 | >10 |
| 2',7-diC12 | >10 | >10 | >10 |
| 2',7-diC18 | —* | — | — |
| 7-C6 | 0.032 +/− 0.002 | 0.027 +/− 0.019 | 0.091 +/− 0.019 |
| 7-C12 | 4.71 +/− 0.25 | >10 | 7.89 +/− 0.37 |
| 7-C18 | >10 | >10 | >10 |

*Not soluble in DMSO or EtOH.

TABLE 6

GROWTH INHIBITION BY LIPOSOMAL (POPC) PACLITAXELS

| Taxane | A549 | MCF7 | LEWIS LUNG |
|---|---|---|---|
| Paclitaxel | 0.002 +/− 0.001 | <0.003 | 0.04 +/− 0.03 |
| 2'-C6 | 0.40 +/− 0.01 | 0.22 +/− 0.01 | 0.86 +/− 0.15 |
| 2'-C12 | 0.37 +/− 0.02 | 0.19 +/− 0.01 | 1.68 +/− 0.70 |
| 2'-C18 | 3.70 +/− 0.28 | 1.21 +/− 0.06 | >10 |
| 2',7-diC6 | >10 | >10 | >10 |
| 2',7-diC12 | >10 | >10 | >10 |
| 2',7-diC18 | >10 | >10 | >10 |
| 7-C6 | 0.031 +/− 0.001 | 0.018 +/− 0.003 | 0.071 +/− 0.001 |
| 7-C12 | 4.36 +/− 0.14 | 4.79 +/− 4.85 | >10 |
| 7-C18 | >10 | >10 | >10 |

What is claimed is:

1. A taxane derivative having the formula:

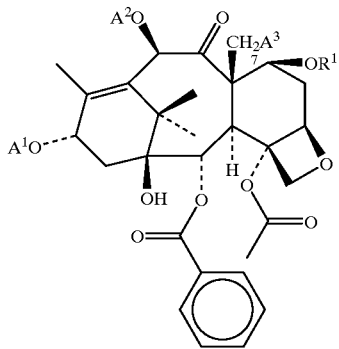

wherein:
A$^1$ is H or a group having the formula Q—C(O)NHCH(C$_6$H$_5$)CH(OR)C(O)—;
Q is C$_6$H$_5$—, (CH$_3$)$_3$C—O— or (CH$_3$)CH=C(CH$_3$)—;
A$^2$ is H or CH$_3$C(O)—;
A$^3$ is H or OH;
R is H, a saturated or unsaturated fatty acid moiety, or a group having the formula Y$^1$, Z$^1$X$^1$, or Z$^1$D$^1$;
R$^1$ is H, a saturated or unsaturated fatty acid moiety, or a group having the formula Y$^2$, Z$^2$X$^2$, or Z$^2$D$^2$;
wherein each of X$^1$ and X$^2$ is independently a group having the formula:

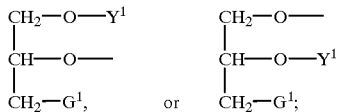

wherein G$^1$ is —OP(O)$_2$OCH$_2$CH$_2$N(CH$_3$)$_3$, —OP(O)$_2$OCH$_2$CH$_2$NH$_2$, —OP(O)$_2$OCH$_2$CH(OH)CH$_2$OH, or —OP(O)$_2$OCH$_2$CH(NH$_2$)CO$_2$H;
wherein each of D$^1$ and D$^2$ is independently a group having the formula:

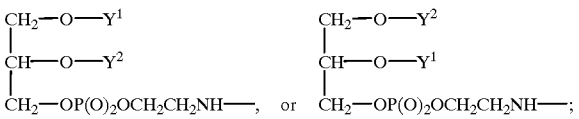

wherein:
each of Y$^1$ and Y$^2$ is independently an acyl chain having 7 to 24 carbon atoms; a group having the formula

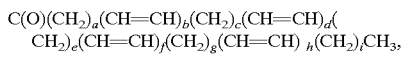

the sum of a+2b+c+2d+e+2f+g+2h+i is equal to an integer of from 7 to 22,
a is zero or an integer from 1 to 22,
each of b, d, f and h is independently zero or 1,
c is zero or an integer from 1 to 20,
e is zero or an integer from 1 to 17,
g is zero or an integer from 1 to 14,
i is zero or an integer from 1 to 11,
a to i can be the same or different at each occurrence;
wherein:
each of Z$^1$ and Z$^2$ is independently a linker of the formula:

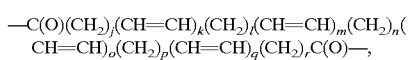

the sum of j+2k+l+2m+n+2o+p+2q+r is equal to an integer from 2 to 22,
each of k, m, o and q is independently zero or 1,
j is zero or an integer from 2 to 22,
l is zero or an integer from 1 to 20,
n is zero or an integer from 1 to 17,
p is zero or an integer from 1 to 14,
r is zero or an integer from 1 to 11,
each of j to r can be the same or different at each occurrence.

wherein when $R^1$ is H, $A^1$ is a group having the formula Q—C(O)NHCH($C_6H_5$)CH(OR)C(O)— and R is not H;

wherein when $A^1$ is H or when $A^1$ is a group having the formula Q—C(O)NHCH($C_6H_5$)CH(OR)C(O)— and R is H, $R^1$ is not H;

and wherein at least one of R and $R^1$ is not H.

2. The taxane derivative of claim 1, wherein at least one of R and $R^1$ is an unsaturated fatty acid moiety.

3. The taxane derivative of claim 2, wherein at least one of R and $R^1$ is an aliphatic fatty acid moiety.

4. The taxane derivative of claim 3, wherein R is an unsaturated aliphatic fatty acid moiety, and $R^1$ is H.

5. The taxane derivative of claim 4, wherein Q is $C_6H_5$—.

6. The taxane derivative of claim 5, wherein $A^2$ is $CH_3C(O)$— and wherein $A^3$ is H.

7. The taxane derivative of claim 1, wherein at least one of R and $R^1$ is a group having the formula $C(O)(CH_2)_a(CH=CH)_b(CH_2)_c(CH=CH)_d[(CH_2)_e(CH=CH)_f]_s(CH_2)_gCH_3$, the sum of a+2b+c+2d+(e+2f)s+g is equal to an integer of from 7 to 22, a is zero or an integer from 1 to 22, each of b, d, and f is independently zero or 1, c is zero or an integer from 1 to 20, e is zero or an integer from 1 to 17, s is zero or an integer from 1 to 7, g is zero or an integer from 1 to 14, and a to g can be the same or different at each occurrence.

8. The taxane derivative of claim 7, wherein $R^1$ is H.

9. The taxane derivative of claim 8, wherein Q is $C_6H_5$.

10. The taxane derivative of claim 9, wherein $A^2$ is $CH_3C(O)$— and wherein $A^3$ is H.

* * * * *